United States Patent
Robert (10) Patent No.: US 9,846,177 B2
(45) Date of Patent: Dec. 19, 2017

(54) METHOD FOR CHECKING A PROBE FOR MEASURING THE PRESSURE OF A FLOW

(71) Applicant: THALES, Neuilly-sur-Seine (FR)

(72) Inventor: François Robert, Chanceaux sur Choisille (FR)

(73) Assignee: THALES, Courbevoie (FR)

( * ) Notice: Subject to any disclaimer, the term of this patent is extended or adjusted under 35 U.S.C. 154(b) by 354 days.

(21) Appl. No.: 14/555,920

(22) Filed: Nov. 28, 2014

(65) Prior Publication Data

US 2015/0153383 A1 Jun. 4, 2015

(30) Foreign Application Priority Data

Nov. 29, 2013 (FR) ...................... 13 02781

(51) Int. Cl.
*G01P 21/02* (2006.01)
*G01P 5/16* (2006.01)
*G01N 29/036* (2006.01)

(52) U.S. Cl.
CPC .......... *G01P 21/025* (2013.01); *G01N 29/036* (2013.01); *G01P 5/16* (2013.01)

(58) Field of Classification Search
CPC ...................................... G01P 21/025
See application file for complete search history.

(56) References Cited

U.S. PATENT DOCUMENTS

| | | |
|---|---|---|
| 5,257,536 A | 11/1993 | Biegbeder et al. |
| 2007/0280046 A1 | 12/2007 | Perez |
| 2012/0118037 A1 | 5/2012 | Leblond et al. |

FOREIGN PATENT DOCUMENTS

| | | |
|---|---|---|
| FR | 2665539 A1 | 2/1992 |
| FR | 2959822 A1 | 11/2011 |
| GB | 2478522 A | 9/2011 |

*Primary Examiner* — Robert R Raevis
(74) *Attorney, Agent, or Firm* — Baker & Hostetler LLP (57) ABSTRACT

A method for detecting the blocking of a drain hole of a pressure measurement probe by means of an acoustic checking device, the probe comprising an internal volume provided with at least one drain hole communicating with the outside of the volume, the checking device being able to be connected to the internal volume of the probe and comprising means for measuring an acoustic imprint of the internal volume. The method comprises: measuring an acoustic imprint by plugging the at least one drain hole from the outside of the volume; measuring an acoustic imprint without plugging the at least one drain hole from the outside of the volume; and comparing the two measured acoustic imprints.

11 Claims, 5 Drawing Sheets

METHOD FOR CHECKING A PROBE FOR MEASURING THE PRESSURE OF A FLOW

CROSS-REFERENCE TO RELATED APPLICATION

This application claims priority to foreign French patent application No. FR 1302781, filed on Nov. 29, 2013, the disclosure of which is incorporated by reference in its entirety.

FIELD OF THE INVENTION

The invention relates to a method for checking a probe for measuring the pressure of a flow. The invention is particularly useful in the field of pressure probes implemented in the aeronautical field.

BACKGROUND

In effect, piloting any aircraft entails knowing its relative speed in relation to the air, that is to say to the relative wind. This speed is determined using probes for measuring the static pressure Ps and the total pressure Pt. The total Pt and static Ps pressures provide the modulus of this speed vector.

Figure 1:
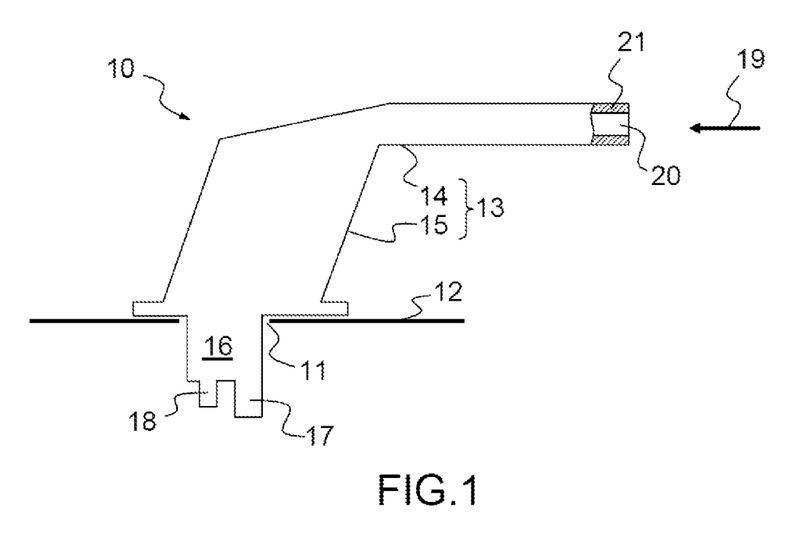
FIG. 1, already presented, represents a total pressure measurement probe according to the prior known art, FIGS. 2a and 2b, already presented, represent two views of the probe of FIG. 1 in the vicinity of which is positioned a checking device according to the prior known art.

As is known, the total pressure Pt can be measured using a so-called Pitot tube. This is a tube that is open at one of its ends and blocked at the other. The open end of the tube faces substantially into the flow. The stream of air situated upstream of the tube is progressively slowed down until it reaches an almost zero speed at the inlet of the tube. The slowing down of the speed of this stream of air increases its pressure. This increased pressure forms the total pressure Pt of the flow of air. The principle of such a total pressure measurement probe is recalled by FIG. 1. The probe 10 is intended to be fixed through an opening 11 produced in the skin 12 of an aircraft. The probe 10 comprises a part 13 external to the skin 12 and formed by a Pitot tube 14 borne by a strut 15. The probe 10 also comprises an internal part 16 essentially comprising an electrical connector 17 and a pneumatic connector 18. The connector 17 makes it possible to electrically connect the probe 10 to the aircraft, for example to connect heating means for the de-icing of the probe 10. The connector 18 allows for the pneumatic connection of the Pitot tube 14 to a pressure sensor or other measurement device, situated inside the skin 12 of the aircraft. The probe 10 is positioned on the skin 12 of the aircraft such that the Pitot tube 14 is oriented substantially along a longitudinal axis of the aircraft, excluding the laminar boundary layer, for the direction of flow, embodied by an arrow 19, to substantially face an inlet orifice 20 situated at a first end 21 of the Pitot tube 14. In the example represented, the Pitot tube 14 is fixed relative to the skin 12 of the aircraft. It is of course possible to mount the Pitot tube 14 on a mobile strut such as, for example, a paddle that can be oriented in the axis of the flow as for example described in the patent published under the number FR 2 665 539.

Figure 2A:
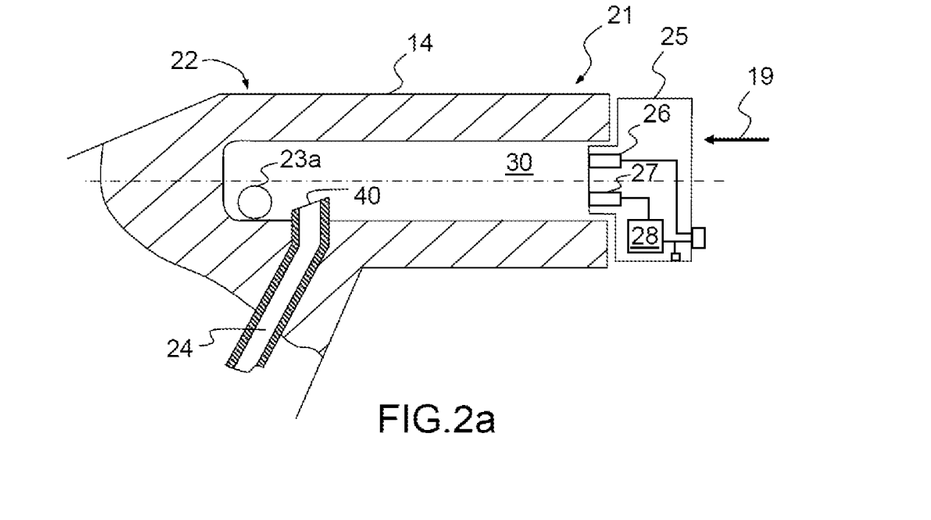
Figure 2B:
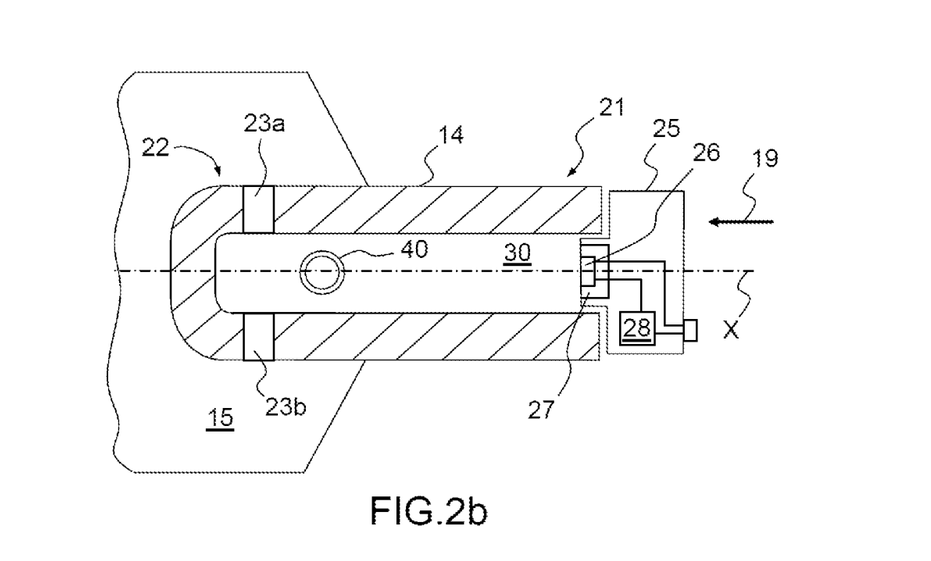

In practice, the flow of air can convey solid or liquid particles, such as, for example, water from the clouds, likely to penetrate into the Pitot tube and to build up in the tube at the blocked end. To prevent such a build-up from disturbing the pressure measurement, one or more drain holes and also water traps are generally provided, to avoid any risk of blocking of the ducts responsible for transmitting the total pressure to the pressure sensors situated inside the skin of the aircraft or to the instruments of the aircraft instrument panel. As represented in FIGS. 2a and 2b, the Pitot tube 14 thus comprises, in proximity to an end 22, one or more drain holes 23a and 23b that make it possible to discharge particles likely to penetrate into the tube 14. Still at the end 22 of the tube, an air line 24 opens into the tube 14 to there form a pressure tap 40 at which the air pressure is to be measured. The pressure tap 40 is generally constructed in such a way as to avoid the ingestion of water into the tube 14 and thus form a water trap. The line 24 is, for example, linked to a pressure sensor that is not represented in FIG. 2. The pressure sensor makes it possible to effectively measure the pressure of the air prevailing inside the tube 14 at its end 22. Apart from the drain hole or holes, whose sections are small compared to that of the tube 14, the tube 14 is closed at its end 22. The pressure measured at this end therefore represents the total pressure Pt of the flow of air.

The drain holes make it possible to discharge the liquids and any particles that might penetrate into the tube. The slowing down of the air in the tube is not therefore complete and the total pressure Pt measurement is thereby affected. More specifically, the greater the effort to avoid the build-up of water or of particles of significant size, the more the total pressure measurement is thereby affected by increasing the dimensions or the number of drain holes. Conversely, the greater the effort to enhance the total pressure Pt measurement by reducing the dimensions or the number of drain holes, the greater the risk of build-up of water or of particles. With a Pitot tube, there therefore has to be a trade-off between quality of the total pressure Pt measurement and risk of disturbance of the measurement because of the penetration of water, and of particles conveyed by the flow of air where the measurement is performed.

In the operational life of aircraft, the drain holes can be polluted, because of the ingestion of dust, insects, plant residues or other foreign bodies. Because of their size and the position of the Pitot tubes on the fuselage of an aircraft, the periodic checking of the integrity of the drain holes is difficult.

The checking of the drain holes of the Pitot tubes is generally done visually. The operator responsible for the maintenance of the aeroplanes inspects the drain hole or holes using a small lamp. If foreign bodies are observed, the probe is dismantled, and its pneumatic circuits cleaned. This operation is all the more difficult when the aeroplane is of large size. Access to the probe and to the drain holes whose diameter is generally less than 1 mm is difficult.

Also known from the applicant is a checking device intended to be connected temporarily to the pressure measurement probe, and that makes it possible to check, using an acoustic transmitter and an acoustic receiver, the non-blocking of the internal cavities and of the drain holes of the probe. The principle of such a device is notably described by the patent published under the reference FR 2 959 822. FIGS. 2a and 2b of this application also recall this principle. The checking device 25 comprises a transmitter 26 and a receiver 27 intended to be connected to an internal volume 30 of the probe, formed by the inside of the tube 14, the drain hole or holes 23a and 23b, and the line 24. The transmitter transmits an acoustic signal that is propagated in the internal volume 30 and the receiver is configured to pick up an acoustic signal observed in the internal volume 30. The device also comprises processing means 28 that make it possible to compare the acoustic signal observed in the internal volume to a reference acoustic signal measured on a non-clogged probe, in order to establish the presence of particles in the internal volume.

The comparison of the acoustic signal measured during a periodic maintenance operation to a predefined reference acoustic signal in practice comes up against a number of difficulties. The acoustic signal picked up by the receiver is greatly dependent on the conditions of the measurement. For example, the ambient temperature which affects the propagation of the acoustic signal directly impacts on the effectiveness of the comparison. Dispersions, even when they are limited, in the geometry of the internal volume also impact on the measured acoustic signal. The direct comparison of an acoustic measurement performed during a maintenance operation for a probe mounted on an aircraft, with an acoustic signal measured in a laboratory on a reference probe does not make it possible to effectively detect the blocking of the drain holes of a pressure measurement probe.

SUMMARY OF THE INVENTION

The present invention relates to a method for detecting blocking of a drain hole that mitigates the drawbacks of the solutions hitherto envisaged.

To this end, the subject of the invention is a method for detecting the blocking of a drain hole of a pressure measurement probe by means of an acoustic checking device; the probe comprising an internal volume provided with at least one drain hole communicating with the outside of the volume; the checking device being able to be connected to the internal volume of the probe and comprising means for measuring an acoustic imprint of the internal volume. The method comprises steps consisting in:

measuring an acoustic imprint by plugging the at least one drain hole from outside the volume,
measuring an acoustic imprint without pluging the at least one drain hole from outside the volume,
comparing the two measured acoustic imprints.

Advantageously, the method comprises a preliminary step consisting in connecting the acoustic checking device to the probe.

Advantageously, the at least one drain hole is plugged by a manual intervention of an operator directly on the probe.

Advantageously, the method comprises intermediate steps of displaying instructions intended for an operator, consisting in requesting the triggering of an acoustic imprint measurement by means of the checking device, and/or the plugging of the at least one drain hole of the probe.

Advantageously, the method comprises a step of displaying the comparison of the measured acoustic imprints, and/or a report of the blocking of the at least one drain hole.

Advantageously, the comparison step consists in comparing the acoustic imprints measured for a predefined resonance frequency or a predefined frequency range.

Advantageously, the measurement means of the checking device comprise an acoustic transmitter and an acoustic receiver that can be connected to the internal volume in such a way that the transmitter transmits an acoustic signal that is propagated in the internal volume and in such a way that the receiver picks up an acoustic signal observed in the internal volume.

According to a particular aspect of the invention, the internal volume of the probe is provided with two drain holes. The probe and the checking device are configured in such a way that the acoustic imprint measured by pluging only a first drain hole from outside the volume is substantially identical to the acoustic imprint measured by pluging only a second drain hole from outside the volume. In a first implementation, the method comprises steps consisting in:

measuring an acoustic imprint by plugging only the first drain hole,
measuring an acoustic imprint by plugging only the second drain hole,
measuring an acoustic imprint without pluging the two drain holes,
comparing the three measured acoustic imprints.

In an alternative implementation, the method comprises steps consisting in:

measuring an acoustic imprint by simultaneously plugging both drain holes,
measuring an acoustic imprint without plugging both drain holes,
comparing both measured acoustic imprints.

BRIEF DESCRIPTION OF THE DRAWINGS

The invention will be better understood and other advantages will become apparent on reading the detailed description of embodiments given by way of example in the following figures.

In the interests of clarity, the same elements bear the same references in the different figures.

DETAILED DESCRIPTION

The invention is described in relation to a total pressure measurement probe, similar to that described previously by FIG. 1. It is theoretically possible to implement it for a static pressure measurement probe, for a Pitot/static probe or for a probe of totally or partially pneumatic incidence. Generally, the device according to the invention is intended for the checking of a probe comprising an internal volume provided with at least one drain hole communicating with the outside of the volume. In the case of the total pressure probe represented in FIGS. 2a and 2b, the internal volume 30 of the probe comprises the inside of the Pitot tube 14, two drain holes 23a and 23b, and the line 24 for example linked to a pressure sensor.

The method implements an acoustic checking device that can be connected to the internal volume of the probe. The device can be connected to the probe temporarily, for example by an operator during a maintenance operation. The connection can also be permanent, the device for example forming an integral part of the probe. The device comprises measurement means 25 configured to measure an acoustic imprint of the internal volume 30 of the probe. For this, the measurement means 25 comprise an acoustic transmitter 26 capable of transmitting an acoustic signal that is propagated in the internal volume 30, and a receiver 27 capable of picking up an acoustic signal observed in the internal volume 30. The acoustic signal transmitted by the transmitter can be the acoustic signal obtained by sweeping a given frequency band, also known by the term chirp. The acoustic signal observed by the receiver in response to this transmitted frequency ramp then constitutes the acoustic imprint of the volume. An acoustic imprint measurement by the checking device can be triggered on the request of an operator. The measurement consists in transmitting the acoustic signal that is propagated in the internal volume, in picking up the acoustic signal observed in the volume, and in storing this acoustic signal picked up by the receiver.

The invention relates to a method for detecting the blocking of a drain hole of a pressure measurement probe by means of the checking device. The general idea of the invention consists in measuring the acoustic imprint of the probe by deliberately plugging one or more drain holes. The drain holes can, for example, be plugged from the outside, directly on the probe, by a maintenance operator. The detection is then based on the comparison of this imprint with an imprint measured without plugging the drain hole or holes.

Note that FIGS. 2a and 2b represent a widely used architecture of a probe comprising two identical drain holes formed facing one another in the Pitot tube. The checking device can be connected to the probe by the end 21 of the Pitot tube, and configured in such a way that the acoustic signal transmitted through the inlet orifice 20 forms a planar wave that is propagated in the tube along its main axis referenced X. In this configuration of the probe and of the device, the acoustic imprints measured by the device are identical for both drain holes. In other words, the imprint measured by plugging only a first drain hole is substantially identical to the acoustic imprint measured by plugging, from the outside, only a second drain hole. The invention is described hereinbelow in relation to this particular configuration. Obviously, the method according to the invention is not limited to this configuration but is applicable more generally to a probe comprising an internal volume provided with at least one drain hole communicating with the outside, and a device that can be connected to the internal volume and comprising means for measuring an acoustic imprint of the internal volume.

Figure 3A:
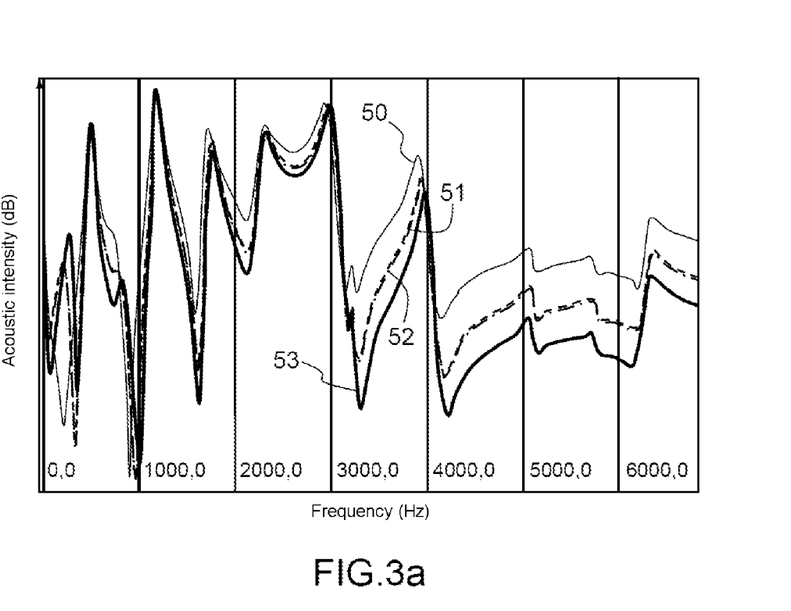
FIGS. 3a and 3b illustrate the principle of the method according to the invention for detecting the blocking of a drain hole of a pressure measurement probe by means of the device.
Figure 3B:
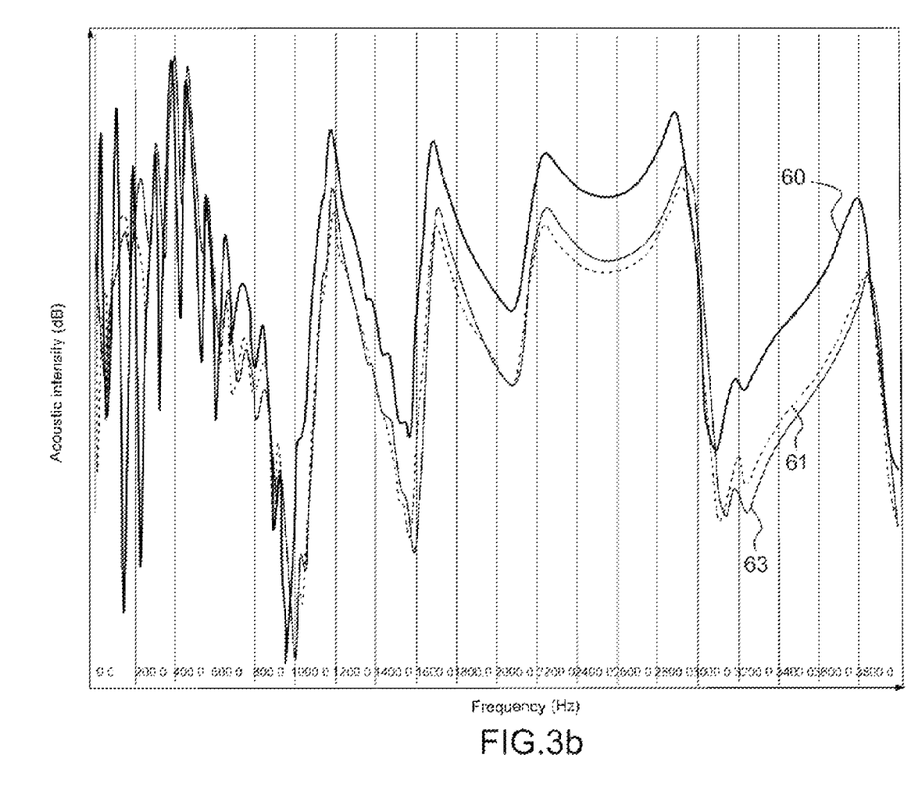

FIGS. 3a and 3b illustrate the principle of the method for detecting the blocking of a drain hole according to the invention.

FIG. 3a represents four acoustic signals measured for one and the same probe and by means of the device 25. The intensity of the measured acoustic signal is represented as a function of the frequency. The transmitted acoustic signal is obtained by sweeping an increasing frequency band between 0 and 7000 Hz.

The acoustic signal referenced 50 corresponds to the acoustic imprint measured in the case where both drain holes 23a and 23b are plugged. The acoustic signal referenced 51 corresponds to the acoustic imprint measured in the case where a first drain hole, for example 23a, called "right" hole, is plugged. The acoustic signal referenced 52 corresponds to the case where a second drain hole, for example 23b, called "left" hole, is plugged. Finally, the acoustic signal referenced 53 corresponds to the case where neither of the two drain holes 23a and 23b, is plugged. For these measurements, the probe is not clogged, the internal volume does not contain any particles likely to block the drain holes. The two drain holes exhibit the same internal geometry. Logically, the acoustic signal 51 measured by plugging the right hole is substantially identical to the acoustic signal 52 measured by plugging the left hole. It is found, on the other hand, that these two signals are clearly distinguished from the acoustic signal 53 measured in the case where the right hole and the left hole are not plugged.

The principle of detecting the blocking of a drain hole is to compare an acoustic imprint measured by deliberately plugging the drain hole from the outside of the probe, with an acoustic imprint measured without plugging this drain hole. By comparing the signals around a particular resonance frequency, the method can conclude that the drain hole is actually blocked when the two signals are identical, or that it is not blocked when the signals differ by a value greater than a predefined threshold. The detection method can be enhanced in various ways to improve its efficiency. For example, for a probe with two drain holes, the acoustic imprints measured by plugging only the right hole then only the left hole can be compared together, or compared to the imprint measured in the case where neither of the holes is plugged. Several implementations of the method are detailed hereinbelow.

FIG. 3b shows three acoustic signals measured for one and the same probe and by means of the checking device 25. As for the preceding figure, the intensity of the measured acoustic signal is represented as a function of the frequency. The acoustic signal transmitted is obtained by sweeping an increasing frequency band between 0 and 4000 Hz.

The probe implemented for the measurement of the signals represented in FIG. 3b is not identical to that implemented for FIG. 3a. The internal volume of the two probes comprises the same Pitot tube and the same two drain holes. However, the air line 24 linking the inside of the tube to the pressure sensor does not exhibit the same architecture for the two probes. Typically, the line 24 consisting of a flexible material tube has a length substantially greater for the probe of FIG. 3a compared to that of the probe of FIG. 3b.

The acoustic signal referenced 60 corresponds to the acoustic imprint measured in the case where both drain holes 23a and 23b are plugged. The acoustic signal referenced 61 corresponds to the acoustic imprint measured in the case where one drain hole is plugged, for example the right hole. The acoustic signal referenced 63 corresponds to the case where neither of the two drain holes 23a and 23b is plugged.

It is found that the acoustic imprint is greatly impacted by the modification of the geometry of the internal volume. The acoustic signals measured at low frequency, typically between 0 and 1000 Hz differ very greatly between FIGS. 3a and 3b. It is also found that the signals 60, 61 and 63 are very clearly distinguished from one another, particularly in the area of the high frequencies, beyond 1000 Hz. These two observations highlight the limits of the known solutions and the benefit of the method envisaged by the invention.

The measurement of the acoustic imprint is sensitive to any alteration of the geometry of the internal volume, such that it is difficult to effectively identify the blocking of a drain hole by comparing the acoustic signal measured on an operational probe with a signal measured on a reference probe; a deviation between these two signals also potentially resulting from a manufacturing dispersion of the probe, from a clogging of the probe outside of the drain holes, or even from a modification of the operating conditions (difference in ambient temperature).

In the method envisaged by the invention, the comparison relates, on the contrary, to acoustic imprints measured for one and the same probe, taken in the same conditions. The deviations between the signals are essentially linked to an alteration of the geometry of the drain holes. It becomes possible to effectively detect the blocking of a drain hole.

Figure 4:
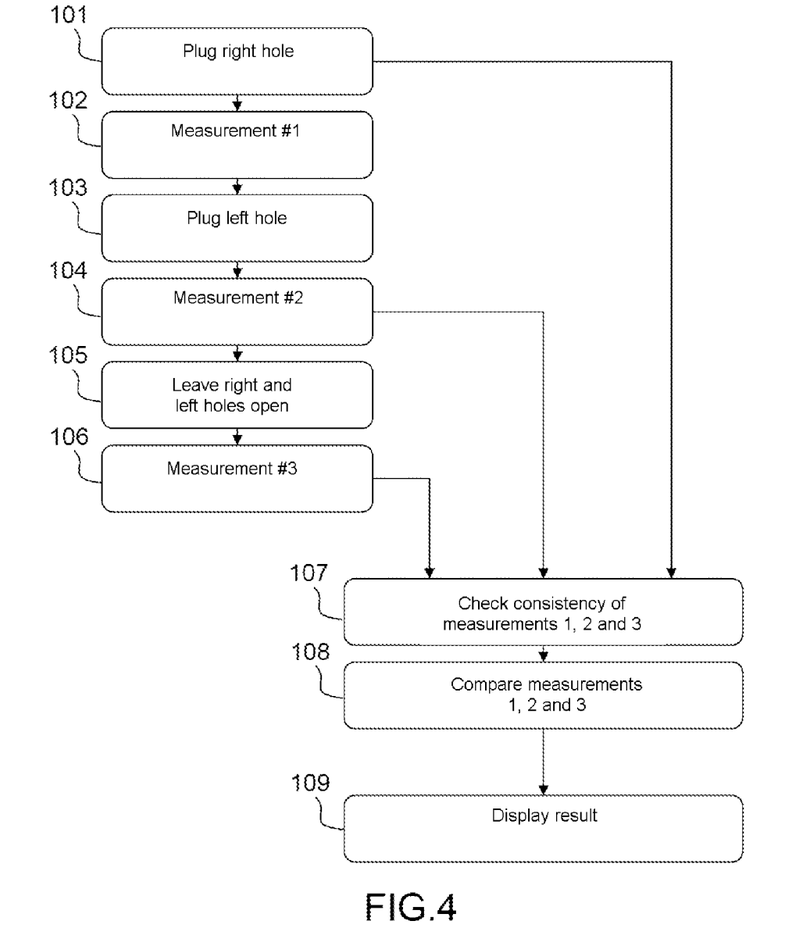
FIG. 4 represents, in the form of a flow diagram, an exemplary detection method according to the invention.

FIG. 4 represents, in flow diagram form, an exemplary detection method according to the invention. This exemplary method is applicable to the case of a probe with two drain holes as mentioned previously. The method thus comprises steps referenced 102, 104, 106 and 108, respectively consisting in:

measuring an acoustic imprint by plugging a first drain hole, measuring an acoustic imprint by plugging a second drain hole, measuring an acoustic imprint by plugging neither of the two holes, comparing the three measured acoustic imprints.

In a preferred implementation, the two holes are plugged manually by an operator, directly on the probe. In this case, the measurement of an acoustic imprint is also triggered by the operator. The method then comprises the intermediate steps 101, 103 and 105 of transmission of instructions to the operator, consisting in requesting the plugging of one or more drain holes and/or the triggering of the acoustic imprint measurement. Transmitting the instructions to the operator by display by means of a control screen, or even by an audible device, is envisaged.

Note that the order of the three measurement steps 102, 104 and 106 can be modified. On completion of the three measurement steps, a step 107 checks the consistency of the acoustic signals stored in the three measurements. The method can be interrupted at the end of this step if an inconsistency is detected.

On completion of the comparison step 108, the method can also comprise a step 109 of displaying the comparison of the three measurements, or more directly the result of this comparison through a report of the blocking or non-blocking of the drain holes.

A number of embodiments are envisaged for the step 108 of comparing the acoustic imprint measurements. In the case of a probe provided with a single drain hole, the step consists simply in comparing the acoustic signal measured by plugging this hole to the acoustic signal measured without plugging it. More specifically, the step can be configured to compare the two acoustic imprints measured for a predefined resonance frequency or, more broadly, a predefined frequency range, and conclude that a drain hole is blocked if the two imprints differ by a value below a predefined threshold.

In the case of a probe provided with two drain holes, the step 108 can comprise the following substeps consisting in:

comparing the imprint 51 (right hole plugged) to the imprint 53 (holes not plugged)

comparing the imprint 52 (left hole plugged) to the imprint 53 (holes not plugged)

comparing the imprint 51 (right hole plugged) to the imprint 52 (left hole plugged)

The first two substeps make it possible to conclude on the blocking of the drain hole concerned, respectively the right hole and the left hole, in the case where the compared imprints are identical, to within a predefined tolerance. The third substep makes it possible to check the consistency of the measurements in the case where the compared imprints differ from one another beyond the predefined tolerance.

In an alternative implementation of the method, the step 108 can comprise the following substeps consisting in:

comparing the imprint 51 (right hole plugged) to the imprint 53 (holes not plugged)

comparing the imprint 50 (right and left holes plugged) to the imprint 53 (holes not plugged)

comparing the imprint 51 (right hole plugged) to the imprint 50 (right and left holes plugged).

This alternative implementation of the comparison step also makes it possible to conclude on a blocking of one or both of the drain holes. Combining these two implementations in one and the same method for detecting the blocking of a drain hole is also envisaged.

Finally, in another implementation of the method, applicable to the case of a probe with two drain holes, the method can comprise steps consisting in:

measuring an acoustic imprint by simultaneously plugging the drain holes, measuring an acoustic imprint by plugging neither of the two holes, comparing the two measured acoustic imprints.

The comparison of the two imprints for a predefined resonance frequency makes it possible to determine whether the probe is exhibiting a blocking of the drain holes, likely to affect its operation. This last implementation is, however, less accurate. It does not make it possible to determine which drain hole is plugged.

The invention claimed is:

1. A method for detecting the blocking of a drain hole of a pressure measurement probe using an acoustic checking device, the probe comprising an internal volume provided with at least one drain hole communicating with the internal volume, the acoustic checking device being able to be connected to the internal volume of the probe and comprising at least an acoustic receiver; the method comprising:

intentionally plugging the at least one drain hole from outside the internal volume, measuring a first measured acoustic signal when said at least one drain hole is intentionally plugged, measuring a second measured acoustic signal without intentionally plugging said at least one drain hole from outside the internal volume, and comparing the first and second measured acoustic signals.

2. The method according to claim 1, comprising connecting the acoustic checking device to the probe.

3. The method according to claim 1, wherein said at least one drain hole is plugged by a manual intervention of an operator directly on the probe.

4. The method according to claim 1, comprising intermediate steps of displaying instructions intended for an operator, consisting in requesting triggering measurement of the first or second measured acoustic signal by the checking device, and/or plugging of the at least one drain hole of the probe.

5. The method according to claim 1, comprising a step of displaying a comparison of the first and second measured acoustic signals, and/or a report of the blocking of the at least one drain hole.

6. The method according to claim 1, wherein the first and second measured acoustic signals are compared at a predefined resonance frequency or within a predefined frequency range.

7. The method according to claim 1, wherein the acoustic checking device further comprises an acoustic transmitter which transmits at least one transmitted acoustic signal that is propagated in the internal volume such that the acoustic receiver picks up the first or second measured acoustic signal observed in the internal volume.

8. The method according to claim 1, wherein the at least one drain hole comprises a first drain hole and a second drain hole, wherein the first measured acoustic signal is measured when intentionally plugging only the first drain hole from outside the internal volume;

the method further comprising:

intentionally plugging only the second drain hole from outside the internal volume; measuring a third measured acoustic signal when only the second drain hole is intentionally plugged, wherein the probe and the acoustic checking device are configured such that the first measured acoustic signal and the third measured acoustic signal are substantially identical, wherein the second measured acoustic signal is measured without intentionally plugging the first drain hole and the second drain hole, and comparing the first, second, and third measured acoustic signals.

9. The method according to claim 8, wherein comparing the first, second, and third measured acoustic signals comprises:

comparing the first measured acoustic signal with the second measured acoustic signal, comparing the third measured acoustic signal with the second measured acoustic signal, and comparing the first measured acoustic signal with the third measured acoustic signal.

10. The method according to claim 1, wherein the at least one drain hole comprises a first drain hole and a second drain hole and the first measured acoustic signal is measured when intentionally plugging only the first drain hole from outside the internal volume further comprising:

intentionally plugging both the first drain hole and the second drain hole, measuring a third measured acoustic signal when both the first drain hole and the second drain hole are plugged, comparing the first measured acoustic signal with the second measured acoustic signal, comparing the third measured acoustic signal with the second measured acoustic signal, and comparing the first measured acoustic signal with the third measured acoustic signal.

11. The method according to claim 1, wherein the at least one drain hole comprises a first drain hole and a second drain hole, wherein the first measured acoustic signal is measured when intentionally plugging only the first drain hole from outside of the internal volume, and a third measured acoustic signal is measured when intentionally plugging only the second drain hole from outside of the internal volume, the probe and the checking device being configured such that the first measured acoustic signal and the second measured acoustic signal are substantially identical;

the method further comprising intentionally plugging both the first drain hole and the second drain hole, measuring a fourth measured acoustic signal when both the first drain hole and the second drain hole are plugged, wherein the second measured acoustic imprint signal is measured without intentionally plugging the first drain hole and the second drain hole, and comparing the fourth measured acoustic signal with the second measured acoustic signal.

* * * * *